United States Patent [19]

Sato et al.

[11] Patent Number: 4,994,619
[45] Date of Patent: Feb. 19, 1991

[54] SUBSTITUTED CYCLIC KETONES, SUBSTITUTED CYCLIC ENONES, AND PROCESS FOR PRODUCING THE SAME

[75] Inventors: Fumie Sato, Fujisawa; Kazutaka Arai; Katsuaki Miyaji, both of Funabashi, all of Japan

[73] Assignee: Nissan Chemical Industries, Ltd., Tokyo, Japan

[21] Appl. No.: 207,549

[22] Filed: Jun. 16, 1988

[30] Foreign Application Priority Data

| Jun. 16, 1987 | [JP] | Japan | 62-149873 |
| Aug. 4, 1987 | [JP] | Japan | 62-194947 |
| Feb. 10, 1988 | [JP] | Japan | 63-29709 |
| Feb. 25, 1988 | [JP] | Japan | 63-43045 |

[51] Int. Cl.$^5$ .................. C07C 323/28; C07C 217/52
[52] U.S. Cl. .................... 564/455; 564/337; 564/384; 564/462; 560/16; 560/19; 560/36; 560/37
[58] Field of Search ............... 564/455, 337, 384, 462; 560/16, 19, 36, 37

[56] References Cited

U.S. PATENT DOCUMENTS

| 4,122,176 | 10/1978 | Katsube et al. | |
| 4,244,890 | 1/1981 | Kane | 564/455 |
| 4,673,759 | 6/1987 | Dalcanala | 564/455 |

FOREIGN PATENT DOCUMENTS

| 0160495 | 4/1985 | European Pat. Off. |
| 0119879 | 4/1901 | Fed. Rep. of Germany |
| 55327 | 8/1966 | Fed. Rep. of Germany |
| 2358781 | 11/1973 | Fed. Rep. of Germany |
| 2550004 | 11/1975 | Fed. Rep. of Germany |
| 3613573 | 4/1986 | Fed. Rep. of Germany |
| 1481067 | 5/1967 | France |
| 1494119 | 9/1967 | France |
| 52-93746 | 8/1977 | Japan |
| 1168080 | 10/1969 | United Kingdom |

OTHER PUBLICATIONS

Weiss, *Journal of Organic Chem.*, vol. 44, p. 1439, 1979.

*Primary Examiner*—Robert A. Wax
*Assistant Examiner*—F. Tsung
*Attorney, Agent, or Firm*—Birch, Stewart, Kolasch & Birch

[57] ABSTRACT

The present invention relates to substituted cyclopentanone and cyclohexanone derivatives and substituted cyclopentenone and cyclohexenone derivatives, which are useful as intermediates for pharmaceutical products and agricultural chemicals and especially useful for the synthesis of prostaglandins, and also to a process for producing the same.

10 Claims, No Drawings

SUBSTITUTED CYCLIC KETONES, SUBSTITUTED CYCLIC ENONES, AND PROCESS FOR PRODUCING THE SAME

BACKGROUND OF THE INVENTION

1. Field of the Invention

The present invention relates to substituted cyclic ketones and substituted cyclic enones, or substituted cyclopentanone and cyclohexanone derivatives and substituted cyclopentenone and cyclchexenone derivatives, which are useful as intermediates for pharmaceutical products and agricultural chemicals and especially useful for the synthesis of prostaglandins, and also to a process for producing the same.

2. Description of the Prior Art

Substituted cyclopentanone derivatives and α-substituted cyclopentenone derivatives are attracting attention because of their usefulness as intermediates for pharmaceutical products and agricultural chemicals. They are useful especially as intermediates for prostaglandins having strong physiological activities.

Heretofore, there are several known processes for producing prostaglandins. According to one of them, prostaglandin E is produced from a cyclopentenone derivative having no substituent at the β position, by the so-called two-component reaction represented by the following equation. (M. J. Weiss, Journal of Organic Chemistry, vol. 44, p. 1439, 1979)

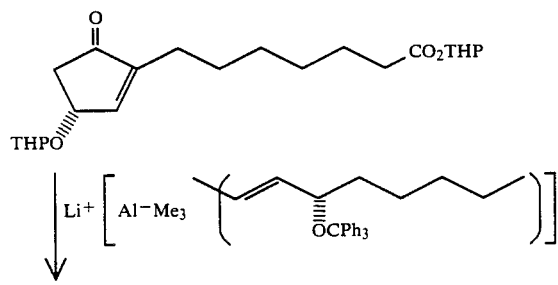

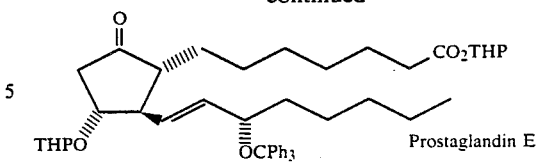

(where THP denotes a tetrahydropyranyl group, Me denotes a methyl group, and Ph denotes a phenyl group.)

There are several known processes for producing intermediates which can be made into such a cyclopentenone derivative having no substituent at the β position ("Prostaglandins and related physiologically active substances", pp. 89-92, 1981, by Terashima, Sakai, and Yamamoto). These processes, however, have some disadvantages when put to industrial use.

The other known processes for producing prostaglandins glandins include the synthesis of prostaglandin $F_{2\alpha}$ by the coupled addition reaction represented by the following equation. [G. Stark et al., J. Am. Chem. Soc., vol. 97, 4745, p. 6260, (1975)]

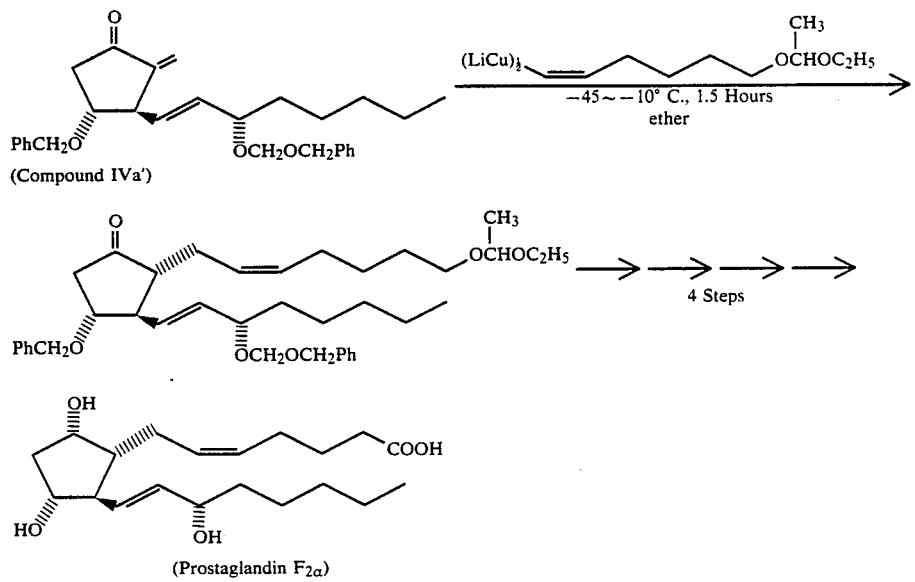

According to the above-mentioned process for synthesis, prostaglandin $F_{2\alpha}$ can be obtained in a high yield from the compound IVa'. In addition, it is possible to change the α chain as desired by properly selecting the reagent for coupled addition.

The known process for producing the compound IVa' has a disadvantage that the yield is low, the reagent used for synthesis is expensive, and usually the resulting compound IVa!]is not optically active but is of racemic modification [D. R. Morton et al., J. Org. Chem., vol. 43, p. 202, (1978); A. P. Kodivsky et al., J. Org. Chem., vol. 49, p. 2301, (1984)]. For this reason, there is a demand for a process for producing prostaglandins in an industrially advantageous manner.

The present invention was completed with the foregoing in mind. Accordingly, it is an object of the present invention to provide new useful substituted cyclopentanone and cyclohexanone derivatives and substituted cyclopentenone and cyclohexenone derivatives from which prostaglandins can be produced in an industrially advanageous manner. It is another object of the present invention to provide a process for producing such derivatives.

In order to achieve the above-mentioned objects, the present inventors carried out a series of researches which led to the findings that those compounds represented by the following formulas are useful as intermediates for the synthesis of prostaglandins.

U denotes ($\alpha$-H, $\beta$-R$^5$) when X is ($\alpha$-OZ, $\beta$-H) and also denotes ($\alpha$-R$^5$, $\beta$-H) when X is ($\alpha$-H, $\beta$-OZ).

n is 1 or 2.

In other words, the present inventors found the following. Upon cyclization of the compound represented by the formula [V] by the aid of a hypohalogenite or a halogen gas in combination with a base, there is obtained the new compound [I], which can be converted

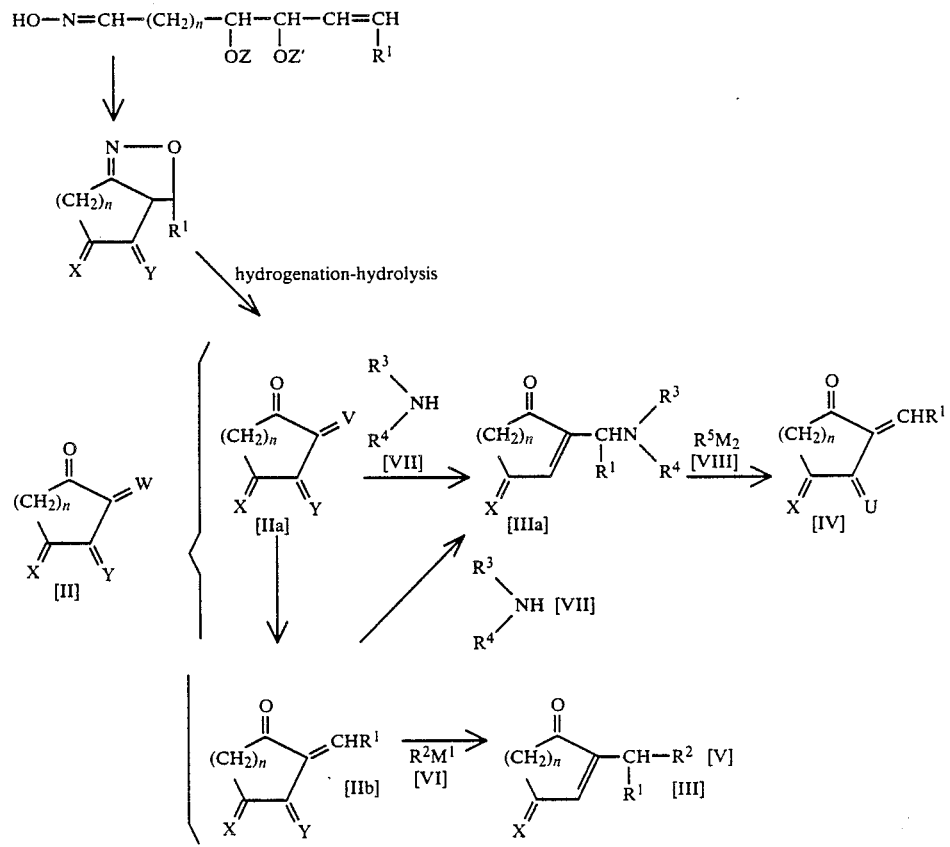

In the above formulas:

R$^1$ denotes a hydrogen atom; a substituted or unsubstituted C$_{1-10}$ alkyl group, alkenyl group, or alkynyl group; or a substituted or unsubstituted phenyl group.

R$^2$ denotes a substituted or unsubstituted C$_{1-10}$ alkyl group, alkenyl group, alkynyl group, alkylthio group, alkylamino group, alkylsilyl group, alkyl tin group, or cyano group.

R$^3$ and R$^4$ each denotes a substituted or unsubstituted C$_{1-10}$ alkyl group; a substituted or unsubstituted phenyl group; and R$^3$ and R$^4$ may be the same or different from each other.

R$^5$ denotes a substituted or unsubstituted C$_{1-15}$ alkyl group, alkenyl group, or alkynyl group.

M$^1$ and M$^2$ each denotes a metal selected from Li, Na, K, Mg, Ca, Ti, Zr, Ni, Cu, Zn, Al, and Sn, or a group containing said metal.

X denotes ($\alpha$-OZ, $\beta$-H) or ($\alpha$-H, $\beta$-OZ).

Y denotes ($\alpha$-OZ', $\beta$-H) or ($\alpha$-H, $\beta$-OZ').

Z and Z' each denotes a hydrogen atom or a protective group for the hydroxyl group; and Z and Z' may be the same or different from each other.

W denotes CHR$^1$, ($\alpha$-CHR$^1$OH, $\beta$-H), or ($\alpha$-H, $\beta$-CHR$^1$OH).

V denotes ($\alpha$-CHR$^1$OH, $\beta$-H), or ($\alpha$-H, $\beta$-CHR$^1$OH).

into another new compound [II] (including [IIa] and [IIb]). To be more specific, upon hydrogenation-hydrolysis of the new compound [I] in the presence of a hydrogenation catalyst, there is obtained the new compound [IIa]. And, upon sulfonylation of the new compound [IIa] in the presence of a base, followed by desulfonation, there is obtained the new compound [IIb].

The present inventors also found the following. Upon reaction of the new compound [IIb] with the compound represented by the formula [VI], there is obtained a compound represented by the formula [III] which includes the new compound [IIIa]. This new compound [IIIa] is obtained by the reaction of the new compound [IIb] with the compound [VII]. This new compound [IIIa] is also obtained by the sulfonylation of the new compound [IIa] in the presence of a base, followed by desulfonation and reaction with a compound of the formula [VII]. Upon reaction of the new compound [IIIa] with a compound represented by the formula [VIII], there is obtained a compound represented by the formula [IV].

The present inventors found that the compounds represented by the formulas [II] ([IIa] and [IIb]), [III], [IIIa], and [IV] are intermediates useful for the synthesis of prostaglandins. These findings led to the present invention.

Accordingly, the present invention provides:
(1) The new compound [I] and a process for producing the same;
(2) the new compounds [II] ([IIa] and [IIb]) and a process for producing the same.
(3) a process for producing the compound [III], and the new compound [IIIa] and a process for producing the same.
(4) a process for producing the compound [IV].

DETAILED DESCRIPTION OF THE INVENTION

The invention will be described in more detail in the following.

The first aspect of the present invention is concerned with a new compound represented by the formula [I] and a process for producing a new compound represented by the formula [I] from a compound represented by the formula [V].

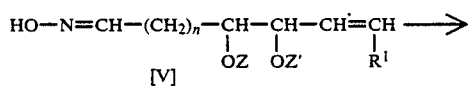

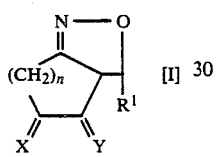

In the formula [I], X denotes ($\alpha$-OZ, $\beta$-H) or ($\alpha$-H, $\beta$-OZ); Y denotes ($\alpha$-OZ', $\beta$-H) or ($\alpha$-H, $\beta$-OZ'); Z and Z' each denotes a hydrogen atom or a protective group for the hydroxyl group; and Z and Z' may be the same or different from each other. $R^1$ denotes a hydrogen atom; a substituted or unsubstituted $C_{1-10}$ alkyl group, alkenyl group, or alkynyl group; or a substituted or unsubstituted phenyl group. n denotes an integer of 1 or 2.

The protective groups Z and Z' for the hydroxyl group include, for example, trialkylsilyl group (such as trimethylsilyl group and t-butyldimethylsilyl group), alkoxyalkyl group (such as methoxymethyl group), aralkyloxyalkyl group (such as benzyloxymethyl group), trityl group, and tetrahydropyranyl (THP) group.

$R^1$ includes, for example, a hydrogen atom, methyl group, ethyl group, n-pentyl group, substituted or unsubstituted $C_{1-10}$ alkyl group, alkenyl group, and alkynyl group represented by the formulas below:

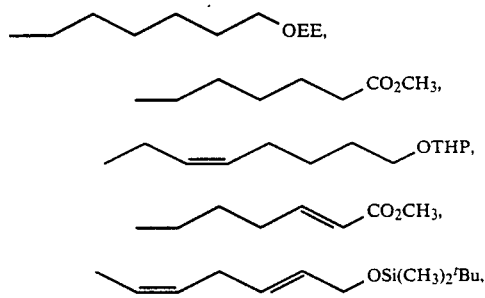

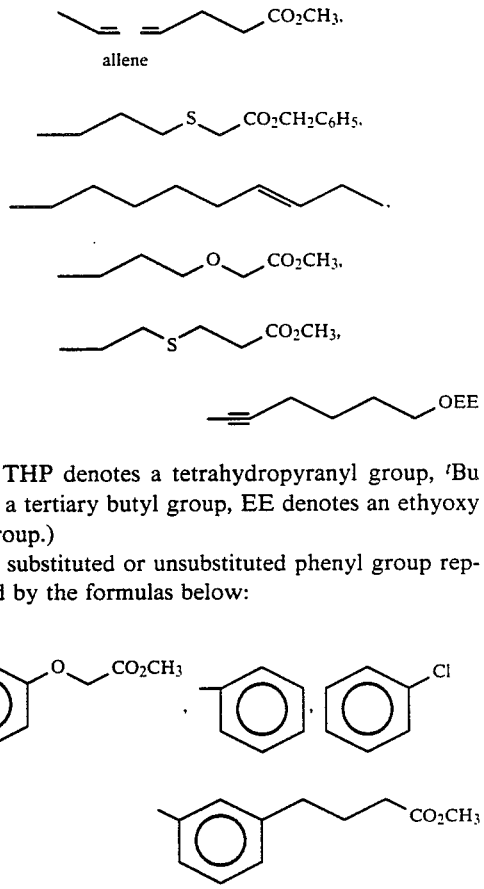

(where THP denotes a tetrahydropyranyl group, $^tBu$ denotes a tertiary butyl group, EE denotes an ethyoxy ethyl group.)

and a substituted or unsubstituted phenyl group represented by the formulas below:

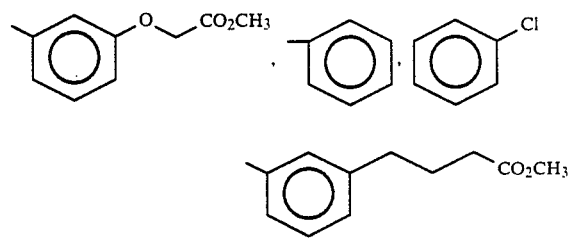

The above-mentioned compound of the formula [I] can be produced by cyclizing the compound of the formula [V] (in which Z, Z', $R^1$, and n are defined as above) with a mild oxidizing agent such as an aqueous solution of hypohalogenite or a halogen gas in combination with a base which converts oxime —CH=N—OH into cyanate —C≡N$^+$—O$^-$.

Examples of the hypohalogenite include sodium hypochlorite, sodium hypobromite, and sodium hypoiodite, with the first being preferred. The hypohalogenite is used in an amount more than an equivalent for the compound of the formula [V] Examples of the halogen gas include chlorine and bromine. The base that can be used for the reaction includes tertiary amines (such as triethylamine), pyridine, and 4-dimethylaminopyridine.

The reaction may be carried out in a solution. Preferred solvents for the solution include halogenated hydrocarbons such as dichloromethane, and hydrocarbons such as hexane, benzene, and toluene.

The reaction temperature and reaction time should be properly selected. The reaction temperature is in the range of $-20°$ C. to the reflux temperature of the solvent, preferably from 0 to 50° C. The reaction time is usually 0.5 to 100 hours.

The second aspect of the present invention is concerned with the new compound represented by the formula [II] ([IIa] and [IIb]) and a process for producing the same.

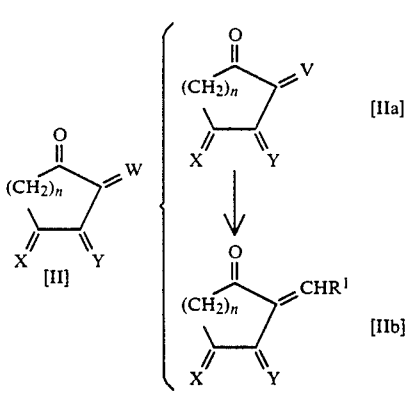

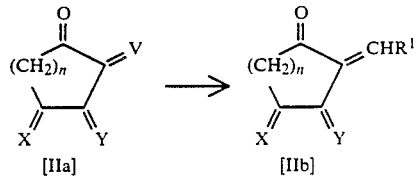

where W denotes CHR$^1$, ($\alpha$-CHR$^1$OH, $\beta$-H), or ($\alpha$-H, $\beta$-CHR$^1$OH), and V denotes ($\alpha$-CHR$^1$OH, $\beta$-H), or ($\alpha$-H, $\beta$-CHR$^1$OH); and X, Y, Z, Z', R$^1$, and n are defined as above.

The new compound of the formula [IIa], which is included in the new compound represented by the formula [II] can be produced by the hydrogenation-hydrolysis of the new compound [I] in the presence of a hydrogenation catalyst.

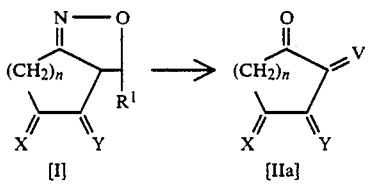

The hydrogenation-hydrolysis is intended to carry out the hydrogenation cleavage and hydrolysis simultaneously under weak acidic conditions in a hydrogen atmosphere using a hydrogenation catalyst.

The hydrogenation catalyst used for this reaction may be any known ones such as Raney nickel, palladium, platinum, palladium/carbon, palladium/alumina, platinum/carbon, and platinum/aluminum.

The above mentioned hydrogenation-hydrolysis should preferably be carried out under weak acidic conditions, especially pH 5~6. For such conditions, it is desirable to add a weak acid such as boric acid and phosphoric acid. The amount of the weak acid should be 1~10 equivalents, preferably 1~5 equivalents.

The above-mentioned reaction should preferably be carried out in a solution. Preferred solvents for the solution include water and a mixed solvent of water and tetrahydrofuran, dioxane, methanol, or ethanol. They are not limitative.

In the above-mentioned reaction, the hydrogen pressure should be in the range of normal pressure to 100 kg/cm$^2$ (gauge), the reaction temperature should be in the range of $-50°$ C. to the boiling point of the solvent, and the reaction time should be in the range of 20 minutes to 15 hours.

The new compound of the formula [IIb], which is included in the new compound represented by the formula [II], can be produced by the sulfonylation of the above-mentioned new compound [IIa] in the presence of a base, followed by desulfonylation.

The base that can be used for the reaction includes tertiary amines (such as triethylamine), pyridine, and 4-dimethylaminopyridine. The sulfonylating agent includes alkylsulfonyl chloride (such as methylsulfonyl chloride) and arylsulfonyl chloride (such as p-toluenesulfonyl chloride). They are used in an amount more than an equivalent Usually, the base is used in excess of the sulfonylating agent.

The above-mentioned sulfonylating reaction and desulfonating reaction may be carried out in a solution. Preferred solvents for the solution include chloroform, methylene chloride, carbon tetrachloride, and diethyl ether. They may be used alone or in combination with one another.

The sulfonylating reaction and desulfonating reaction may be carried out under the conditions for known sulfonylating reaction and desulfonating reaction. The two reactions may be carried out simultaneously or sequentially. In the former case, the desulfonating reaction is carried out, with the reaction product of the sulfonylating reaction left in the reaction system. In the latter case, the desulfonating reaction is carried out after the reaction product of the sulfonylating reaction has been removed. For both the reactions, the reaction temperature should be $-100°$ C. to 100$°$ C. and the reaction time should be 20 minutes to 6 hours.

The third aspect of the present invention is concerned with a process for producing the compound of the formula [III], the new compound [IIIa] included in the formula [III], and a process for producing the new compound [IIIa].

The compound represented by the formula [III] is synthesized by reacting the above-mentioned new compound [IIb] with a nucleophilic reagent represented by the formula [VI].

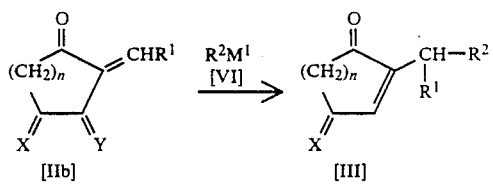

where R$^2$ denotes a group selected from substituted or unsubstituted C$_{1-10}$ alkyl group, alkenyl group, alkynyl group alkylthio group, alkylamino group, alkylsilyl group, alkyl tin group, or cyano group; M$^1$ denotes a metal selected from Li, Na, K. Mg, Ca, T, Zr, Ni, Cu, Zn, Al, and Sn, or a group containing said metal; and R$^1$, X, Y, Z Z', and n are defined as above.

Examples of the nucleophilic reagent [VI] include R$^2$Li, R$^2$MgBr, R$^2$MgI, R$^2$R$^6$CuQLi$_2$, R$^2$CuQLi, R$^2$(R$^6$)$_2$AlQLi, R$^2$(R$^1$)$_2$Al, R$^2$R$^6$CuQLiMgBr, and R$^2$CuQMgBr where R$^6$ denotes a group selected from substituted or unsubstituted C$_{1-10}$ alkyl group, alkenyl group, alkynyl group, alkylthio group, alkylamino group, alkylsilyl group, alkyloxy group, alkylcarbonyl group, and cyano group; R$^2$ and R$^6$ may be the same or different from each other; and Q denotes a halogen atom, cyano group, alkylthio group, arylthio group, or thiocyano group.

Then the compound [IIb] is reacted with the nucleophilic reagent [VI], the latter should be used in an amount of 0.5~4 equivalents, preferably 0.8~1.2 equivalents, for the former.

The reaction may be carried out in a solution. Any solvent may be used for the solution so long as it does not hinder the reaction. Examples of the solvent include tetrahydrofuran, hexane, pentane, and diethyl ether.

The reaction temperature should be $-100 \sim 50°$ C., preferably $-80 \sim 0°$ C., and the reaction time should be 5 minutes to 50 hours.

The present invention covers also the new compound [IIIa] included in the above-mentioned compound [III].

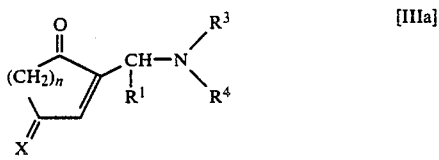

where $R^3$ and $R^4$ each denotes a substituted or unsubstituted $C_{1-10}$ alkyl group or a substituted or unsubstituted phenyl group; $R^3$ and $R^4$ may be the same or different from each other; and $R^1$, X, Z, and n are defined as above.

Examples of $R^3$ and $R^4$ include alkyl groups such as methyl group, ethyl group, n-propyl group, and i-propyl group; substituted alkyl groups such as benzyl group and p-chlorobenzyl group; phenyl group; and substituted phenyl groups such as p-chlorophenyl group.

The above-mentioned new compound [IIIa] is produced by reacting the compound [IIb] with a secondary amine represented by the formula [VII] as the nucleophilic reagent:

where $R^3$ and $R^4$ are defined as above.

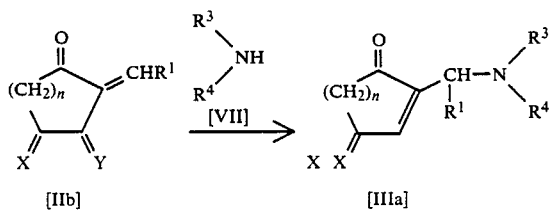

The new compound [IIIa] may also be prepared by sulfonylating the new compound [IIa] in the presence of a base, desulfonating the reaction product, and reacting the reaction product with a secondary amine represented by the formula [VII].

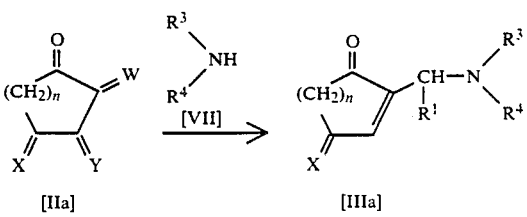

The base and sulfonylating agent that can be used in this reaction are those which are used in the production of the compound [IIb] from the compound [IIa]. The sulfonylating reaction and desulfonating reaction may be carried out in the same manner. The desulfonation reaction product is reacted with a secondary amine [VII] as mentioned above. Examples of the secondary amine [VII] include symmetric amines such as dimethylamine, diethylamine, di-i-propylamine, and diphenylamine; and asymmetric amines such as N-methylaniline and N-ethylaniline.

The desulfonation reaction product may or may not be isolated from the reaction system before its reaction with a secondary amine of the formula [VII]. The reaction may be carried out in a solution. The solvent used for the sulfonylating reaction and desulfonating reaction may be used for this solution. The reaction temperature should be $-100° \sim 100°$ C., or higher than the melting point of the solution and lower than the boiling point of the solution. The reaction time should be 1 hour to 100 hours.

In the meantime, the above-mentioned compound of the formula [III] can be made into prostaglandin E according to the following formula. [Kurozumi et al., Chemical Pharmaceutical Bulletin of Japan, vol. 30, p. 1102, (1982)]

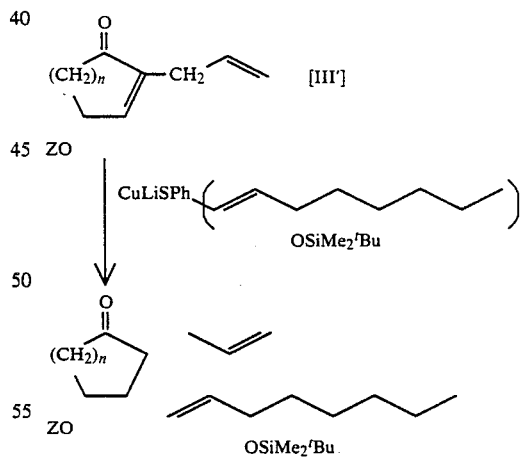

(where Me denotes a methyl group, $^tBu$ denotes a tert-butyl group, and Ph denotes a phenyl group.)

Thus, the compound [IIb] is an effective intermediate for the synthesis of prostaglandin E through the compound [III].

The fourth aspect of the present invention is concerned with a process for producing the compound of the formula [IV] by reacting the above-mentioned new compound [IIIa] with a nucleophilic reagent represented by the formula [VIII].

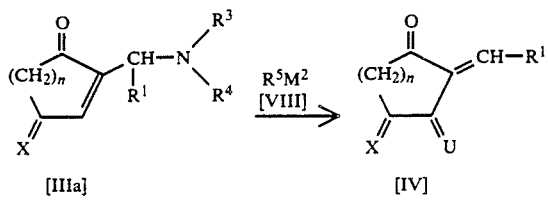

where U denotes (α-H, β-R⁵) when X is (α-OZ, β-H) and also denotes (α-R⁵, α-H) when X is (α-H, β-OZ); R⁵ denotes a group selected from substituted or unsubstituted alkyl group, alkenyl group, and alkynyl group having 1~15 carbon atoms; M² denotes a metal selected from Li, Na, K, Mg, Ca Ti, Zr, Ni. Cu, Zn, Al, and Sn, and a group containing said metal; and X, Z, R¹, R³, and R⁴ are defined above.

Examples of R⁵ include substituted or unsubstituted alkyl groups (such as methyl group, ethyl group, n-propyl group n-octyl group, 4-phenoxybutyl group, and 3-(t-butyldimethylsilyloxy)octyl group); substituted or unsubstituted alkenyl group (such as vinyl group, allyl group, 3-(2-tetrahydropiranyloxy)-1-octen-1-yl group, 3-(t-butyldimethylsilyloxy)-5-methyl-1-nonen-1-yl group, and 3-(benzyloxymethyloxy)-1-octen-1-yl group); and substituted or unsubstituted alkynyl group (such as 1-butynyl group, 1-hexynyl group, 1-octynyl group and 3-(ethoxy-ethyloxy)-1-octen-1 yl group.

For the production of an intermediate for prostaglandins, R⁵ should preferably be a group represented by the formula:

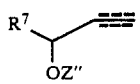

where Z″ denotes a protective group for the hydroxyl group, which may be the same as the above-mentioned protective group Z for the hydroxyl group; the symbol ≣≣≣≣ denotes a single bond, double bond, or triple bond; and R⁷ denotes a substituted or unsubstituted alkyl group having 1 to 10 carbon atoms or an unsubstituted phenyl group.

Examples of R⁷ include a methyl group, ethyl group, n-propyl group, i-propyl group, n-butyl group, i-butyl group, t-butyl group, amyl group, hexyl group, heptyl group, octyl group, nonyl group, decyl group, 2-methylhexy group, 2-methyl-2-hexyl group, 2-hexyl group, cyclopentyl group, cyclohexyl group, cyclohexylmethyl group, hexa-4-in-2-yl group, hepta-4-in-2-yl group, 2,6-dimethyl-hepta-5-en-1-yl group, penta-1-en-1-yl group, penta-2-en-1-yl group, hexa-1-en-2-yl group, 3-ethoxy-2-methyl-propan-2-yl group, ethoxyethyl group, 5-methoxyhexyl group, 6-methoxy-2-hexyl group, halogenated methyl group, halogenated n-butyl group, halogenated n-pentyl group, halogenated nonyl group, phenyl group, benzyl group, halogenated phenyl group, n-pentyloxymethyl group, 1-ethoxy-2-methyl-propan-2-yl group, phenoxymethyl group, benzyloxymethyl group, p-chlorophenoxymethyl group, 2-phenylethyl group, benzyloxyethyl group, p-fluorophenoxymethyl group, phenylacetylenyl group, m-chlorophenoxymethyl group, m-trifluoromethylphenoxymethyl group, 1-butyl-cyclopropyl group, 3-ethyl-cyclopentyl group, benzothiophen-5-yl group, 2-octenyl group, 3-methoxycarbonylpropyl group, and vinyl group.

Examples of M² in the nucleophilic reagent of the formula [VIII] include Li, MgBr, MgI, CuTLi, CuTMgBr, R⁸CuTLi₂, (R⁸)₂AlTLi, (R⁸)₂Al, and R⁸CuTLiMgBr, where R⁸ is a group selected from substituted or unsubstituted C₁₋₁₀ alkyl group, alkenyl group, alkynyl group, alkylthio group, alkylamino group, alkylsilyl group, alkyloxy group, alkylcarbonyl group, 2-thienyl group, and cyano group, and it may be the same as R⁵ mentioned above, and T denotes a halogen atom, cyano group, alkylthio group, arylthio group, or thiocyano group.

M² should preferably be a compound of the formula:

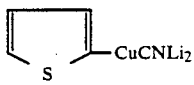

if the compound of the formula [IV], the desired compound in the present invention, is to be produced in high yields.

In the reaction of the compound of the formula [IIIa] with the nucleophilic reagent of the formula [VIII] which is carried out to produce the compound of the formula [IV], the amount of the nucleophilic reagent should be 0.5~4 equivalents, particularly 0.7~1.3 equivalents, for the compound of the formula [IIIa].

This reaction does not necessarily require a solvent; but it is possible to use any solvent so long as it does not interfere with the reaction. Examples of the solvent include tetrahydrofuran, hexane, heptane, and diethyl ether. The reaction should preferably be carried out in a non-oxidative atmosphere, and the atmosphere in the reaction system should preferably be replaced by argon or nitrogen. The reaction temperature should be −100°~50° C., preferably −80°~0° C., and the reaction time should be 5~50 hours, depending on the reaction temperature.

This reaction can be used to produce the compound [IVa] according to the following equation. Since it is possible to produce prostaglandin F₂α from this compound [IVa] as mentioned in the paragraph of prior art, the compound [IIIa] is also useful as an intermediate for the synthesis of prostaglandins.

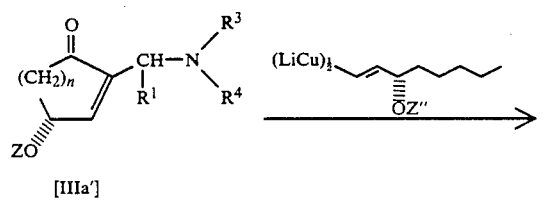

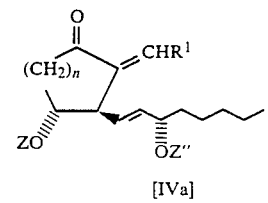

(where Z″ denotes a protective group for the hydroxyl group.)

As mentioned above, the present invention enables the production of the-new compounds [I] and [II] ([IIa], [IIb]), the compound [III] including the new compound [IIIa], and the compound [IV] which are useful as intermediates for the synthesis of prostaglandins.

EXAMPLES

The invention will be described in more detail with reference to the following examples and referential examples, which are not intended to limit the scope of the invention. In the following formulas, Me denotes a methyl group, Et denotes an ethyl group, $^n$Bu denotes an n-butyl group, and $^t$Bu denotes a t-butyl group.

EXAMPLE 1

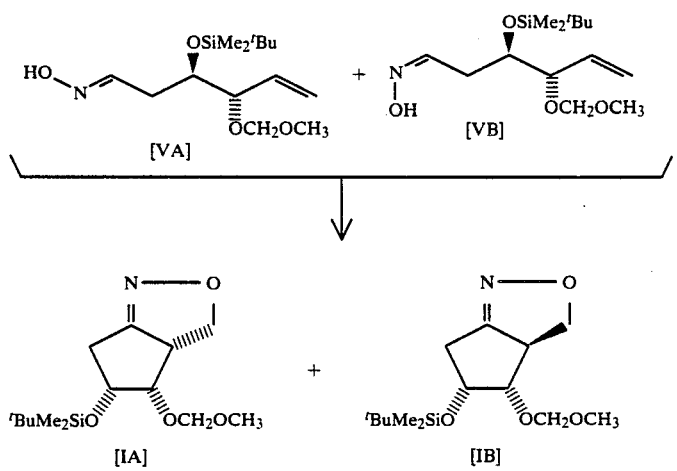

A mixture of the compounds (VA) and (VB) in an amount of 100 mg (0.33 mmol) was dissolved in 6 ml of dichloromethane. To the solution cooled to 0° C. was added dropwise 0.67 ml (0.4 mmol) of an aqueous solution of sodium hypochlorite. After stirring for 10 hours at room temperature and the addition of 5 ml of water, the reaction product was extracted with three 5 ml portions of diethyl ether. The organic layer was dried with anhydrous magnesium sulfate and then concentrated under reduced pressure. The resulting crude product was purified by silica gel chromatography. Thus there was obtained a mixture of the compounds (IA) and (IB) in an amount of 90 mg (0.3 mmol). Yield: 91%.

Analytical values of the mixture of (VA) and (VB):
$^1$H-NMR (CCl$_4$, internal standard: tetramethylsilane) δ0.78 (9H, s), 2.24 and 2.42 (2H, t×2, J=6Hz), 3.17 (3H, s), 3.80 (2H, br, d, J=6Hz), 4.2~4.7 (2H, m), 4.9~6.1 (3H, m), 6.60 and 7.18 (1H, t ×2, J=6Hz), 8.9 and 9.4 (1H, brs ×2).

Analytical values of the mixture of (IA) and (IB):
$^1$H-NMR (CCl$_4$, internal standard: benzene) δ0.06 (s, 6H), 0.86 (s, 9H), 2.10~2.95 (m, 3H), 3.24 (s, 3H), 3.45~4.95 (m, 6H). IR : 1740, 1630, 1460, 1360, 1248, 1130, 1035, 820 cm$^{-1}$.
MS (m/e) : 301 (5, M+), 269 (7), 244 (18), 182 (15), 101 (11), 89 (42), 75 (13), 73 (45), 45 (100). Rf value (silica gel thin-layer chromatography, n-hexane/ethyl acetate =1/1) =0.65 and 0.7

EXAMPLE 2

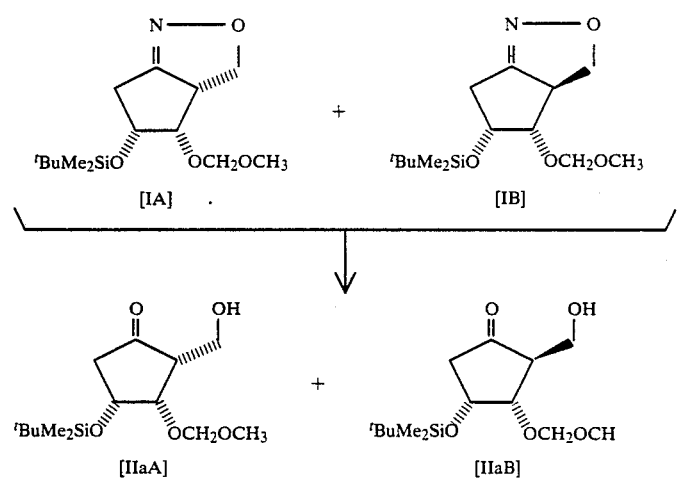

A mixture of the compounds (IA) and (IB) obtained in Example 1, in an amount of 73 mg (0.243 mmol) was dissolved in 6 ml of a 1:5 water-methanol mixture. To the solution were added 30.3 mg (0.49 mmol) of boric acid and 10 mg of 5% palladium/carbon catalyst. The reactants were stirred at 20° C for 3 hours in a hydrogen atmosphere (at normal pressure). The reaction mixture was filtered through silica gel and the filtrate was concentrated under reduced pressure. The resulting crude product was purified by silica gel chromatography. Thus there was obtained a mixture of the compounds (IIaA) and (IIaB) in an amount of 70 mg (0.231 mmol). Yield: 95%.

Analytical values of the mixture of (IIaA) and (IIaB): $^1$H-NMR (CCl$_4$, internal standard: benzene) δ0 10 (s, 6H), 0.85 (s, 9H), 1.93~2.82 (m, 4H), 3.33 (s, 3H), 3.45~4.83 (m, 6H). IR : 425, 1740, 1250, 1040, 830, 775 cm$^{-1}$. MS (m/e) : 273 (2, M+), 243 (4, M+), 186 (17), 185 (100), 157 (13), 143 (17), 89 (11), 75 (20), 73 (14), 45 (69). Rf value (silica gel thin-layer chromatography, n-hexane/ethyl acetate =1/1) =0.65

EXAMPLE 3

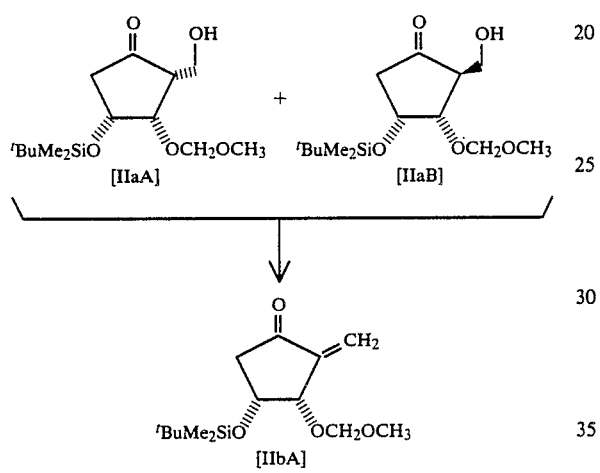

A mixture of the compounds (IIaA) and (IIaB) obtained in Example 2, in an amount of 165 mg (0.545 mmol) was dissolved in 2 ml of dichloromethane. To the solution was added 0.23 ml (1.64 mmol) of triethylamine. To the reactants cooled to 0° C. was added dropwise 0.064 ml (0.82 mmol) of methylsulfonyl chloride with stirring. After stirring at 0° C. for 30 minutes and the addition of 5 ml of saturated sodium chloride solution, the reaction product was extracted with 10 ml of n-hexane. The organic layer was dried with anhydrous magnesium sulfate and then concentrated under reduced pressure. The resulting crude product was purified by silica gel chromatography. Thus there was obtained the compound (IIbA) in an amount of 152 mg (0.53 mmol). Yield: 97%.

Analytical values of the compound (IIbA): $^1$H-NMR (CCl$_4$, internal standard: benzene) δ0.10 (s, 6H), 0.84 (s, 9H), 2.34 (dd, J =1.2, 5Hz, 2H), 3.32 (s, 3H), 4.20~4.51 (m, 2H), 4.63 (dd, J=7.2, 12Hz, 2H), 5.38 and 6.01 (2dd, J =1.7, 2.3Hz, 2H). IR : 1715, 1645, 1460, 1390, 1240, 1045, 817, 775 cm$^{-1}$. Rf value (silica gel thin-layer chromatography, n-hexane/diethyl ether =1/1) =0.65

$^{13}$C-NMR (CCl$_4$) δ 200.9, 144.2, 119.8, 94.5, 77.0, 69.0, 55.2, 45.3, 25.4, 17.8, 5.0.

EXAMPLE 4

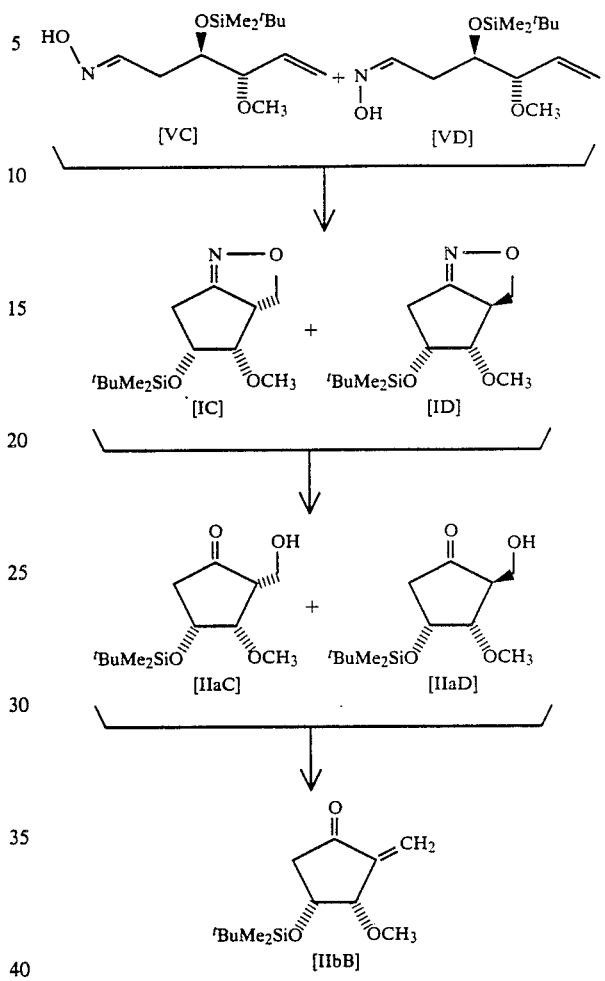

A mixture of the compounds (VC) and (VD) was reacted in the same manner as in Examples 1 and 2 to give a mixture of the compounds (IC) and (ID) and then a mixture of the compounds (IIaC) and (IIbD). Then a mixture of the compounds (IIaC) and (IIaD) was reacted in the same manner as in Example 3 to give the compound (IIbB).

Analytical values of the mixture of (VC) and (VD): $^1$H-NMR (CDCl$_3$, internal standard: tetramethylsilane) δ0.07 (6H, s), 0.87 (9H, s), 2.0~2.9 (2H, m), 3.2 (3H, s), 4.9~6.0 (3H, m), 6.4~4.7 (2H, m), 8.4 (1H, brs).

Analytical values of the compound of (IIbB): $^1$H-NMR (CCl$_4$, internal standard: benzene) δ0.18 (s, 6H), 0.94 (s, 9H), 2.34 (d, J=4.8Hz, 2H), 3.48 (s, 3H), 4.05~4.25 (m, 1H), 4.51 (q, J=5.1Hz, 1H), 5.47 and 6.11 (2brs, 2H). $^{13}$C-NMR (CDCl$_3$) δ201.3, 144.1, 119.8, 82.5, 68.5, 56.6, 45.5, 25.6, 17.9, −4.9. Rf value (silica gel thin-layer chromatography, n-hexane/diethyl ether =1/1) =0.58 [α]$_D^{23}$ −35.4° (C =2.30, CHCl$_3$)

Analytical values of the mixture of (IC) and (ID): $^1$H-NMR (CDCl$_3$, internal standard: tetramethylsilane) δ0.09, 0.11 (6H, s ×2), 0.88 (9H, s), 2.0~2.8 (3H, m), 3.47, 3.56 (3H, s ×2), 3.6~4.2 (3H, m), 4.60 (1H, dt, J=5Hz, 2Hz). IR : 2940, 1470, 1370, 1250, 1140, 1070, 980 cm$^{-1}$. MS(m/e) : 271 (M. 0.5%), 214 (7%), 89 (100%).

Analytical values of the mixture of (IIaC) and (IIaD): $^1$H-NMR (CDCl$_3$, internal standard: tetramethylsilane) δ0.07 (6H, s), 0.89 (9H, s), 1.6~1.9 (3H, m), 3.31 (3H, s), 3.4~4.0 (4H, m). IR (KBr =disk) : 3600-3000, 2900, 1740 cm$^{-1}$. MS (m/e) : 274 (M+ 3%), 217 (7%), 73 (100%).

EXAMPLE 5

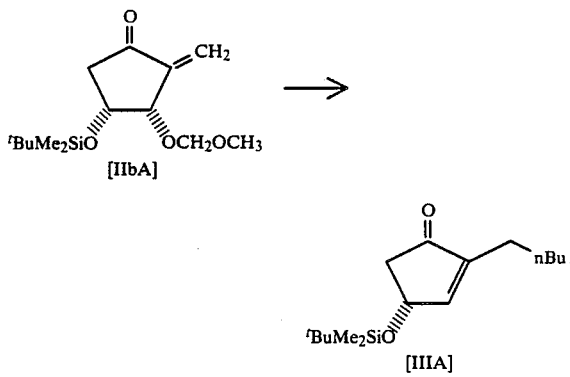

In 3 ml of a 5:1 mixed solvent of tetrahydrofuran and dimethyl sulfide was dissolved 81.7 mg (0.43 mmol) of copper iodide. To this solution cooled to −70° C. was slowly added dropwise 0 56 ml (0.858 mmol) of n-butyl lithium (1.53 mol solution in n-hexane). After stirring for 20 minutes at −70° C., 3 ml of tetrahydrofuran solution containing 113 mg (0.395 mmol) of the compound (IIbA) obtained in Example 3 was slowly added dropwise. After stirring for 20 minutes at −70° C., 6 ml of a saturated aqueous solution of ammonium chloride was added. The reaction mixture was warmed to room temperature and the reaction product was extracted with 7 ml f n-hexane. The organic layer was dried with anhydrous magnesium sulfate and then concentrated under reduced pressure. The resulting crude product was purified by silica gel chromatography. Thus there was obtained the compound (IIIA) in an amount of 110 mg (0.390 mmol). Yield: 99%.

Analytical values of the compound (IIIB): $^1$H-NMR (CCl$_4$, internal standard: benzene) δ0.14 (s, 6H), 0.74~1.10 (m, 12H), 1.13~1.71 (m, 6H), 2.00~2.30 (m, 2H), 2.13 and 2.59 (2dd, J =2.6, 18Hz and J =6.0, 18Hz), 4.72~4.94 (m, 1H), 6.82~6.98 (m, 1H). $^{13}$C-NMR (CCl$_4$) δ205.8, 156.3, 147.2, 69.0, 45.5, 31.5, 27.1, 25.8, 24.3, 22.3, 18.0, 13.8, −4.7. Rf value (silica gel thin-layer chromatography, n-hexane/diethyl ether =8/1) =0.63

EXAMPLES 6 TO 26

The procedure of Example 5 was repeated using a variety of nucleophilic reagents. The reaction conditions and the results are shown in Table 1.

In Table 1, Me denotes a methyl group, Et denotes an ethyl group, $^n$Bu denotes an n-butyl group, $^t$Bu denotes a t-butyl group, EE denotes an ethoxyethyl group, THP denotes a tetrahydropyranyl group, and THF denotes a tetrahydrofuran. The parenthesized number in the column of solvent indicates the ratio by weight of the mixed solvent.

TABLE 1

| Example | Compound of Formula [IIb] | Compound of Formula [VI] ( ) indicates equivalents for Compound [IIb] | Reaction Conditions Solvent | Reaction Conditions Temperature | Reaction Conditions Time | Structural Formula | Compound of Formula [III] | Yields |
|---|---|---|---|---|---|---|---|---|
| 6 | Compound [IIbA] 0.2 g | $^n$BuMgBr (1.1 equiv.) | THF 5 ml | 0° C.~Room temperature | 0.5 Hour | Compound [IIIA] | | 60% |
| 7 | Compound [IIbA] 0.2 g | $^n$BuMgBr (1.8 equiv.) | THF 6 ml | 0° C. | 0.5 Hour | Compound [IIIA] | | 40% |
| 8 | Compound [IIbA] 0.5 g | CuI (1.2 equiv.) + $^n$BuMgBr (1.1 equiv.) | THF (5) + Me$_2$S (1) 20 ml | −78° C. Room temperature | 1 Hour | Compound [IIIA] | | 65% |
| 9 | Compound [IIbA] 0.2 g | CuI (1.3 equiv.) + EEO(CH$_2$)$_6$MgBr (1.1 equiv.) | THF (5) + Me$_2$S (1) 10 ml | −78° C.~0° C. | 1 Hour | | cyclopentenone with (CH$_2$)$_7$OEE and $^t$BuMe$_2$SiO — Compound [IIIB] | 50% |
| 10 | Compound [IIbA] 0.1 g | Et$_3$Al (1.2 equiv.) | THF (1) + Hexane (1) 10 ml | 0° C. | 0.5 Hour | | cyclopentenone with Et and $^t$BuMe$_2$SiO — Compound [IIIC] | 20% |
| 11 | Compound [IIbA] 0.2 g | Li—C≡C—(CH$_2$)$_4$OEE (1.3 equiv.) + Et$_2$AlCl (1.3 equiv.) | Et$_2$O (4) + Hexane (1) 7 ml | 0° C. | 1 Hour | | cyclopentenone with C≡C—(CH$_2$)$_4$OEE and $^t$BuMe$_2$SiO — Compound [IIID] | 30% |
| 12 | Compound [IIbA] 0.2 g | CuI (1.1 equiv.) + $^n$BuLi (2.2 equiv.) | THF 10 ml | −70° C.~0° C. | 1 Hour | Compound [IIIa] | | 95% |
| 13 | Compound [IIbA] 0.2 g | Br(CH$_2$)$_6$OEE (3.7 equiv.) + $^t$BuLi (7.1 equiv.) + CuI (1 equiv.) | Hexane (3) + Et$_2$O (3) THF (5) + Me$_2$S (1) 20 ml | −70° C.~Room temperature | 1 Hour | Compound [IIIB] | | 50% |
| 14 | Compound [IIbA] 0.2 g | (CH$_2$)$_4$OEE vinyl (2.2 equiv.) + $^t$BuLi (4.2 equiv.) + CuI (1.1 equiv.) | Hexane (2) + Et$_2$O (2) + THF (5) + Me$_2$S (1) 20 ml | −70° C.~Room temperature | 1 Hour | | cyclopentenone with CH=CH—(CH$_2$)$_4$OEE and $^t$BuMe$_2$SiO — Compound [IIIE] | 35% |

TABLE 1-continued

| Example | Compound of Formula [IIb] | Compound of Formula [VI] ( ) indicates equivalents for Compound [IIb] | Reaction Conditions | | | Compound of Formula [III] | |
|---|---|---|---|---|---|---|---|
| | | | Solvent | Temperature | Time | Structural Formula | |
| 15 | Compound [IIbA] 0.2 g |  (2.2 equiv.) + <sup>t</sup>BuLi (4.4 equiv.) + CuI (1.1 equiv.) | Hexane (2) + Et₂O (2) + THF (5) + Me₂S (1) 20 ml | −70° C.~Room temperature | 1 Hour |  Compound [IIIF] | 95% |
| 16 | Compound [IIbA] 0.2 g |  (2.2 equiv.) + <sup>t</sup>BuLi (4.0 equiv.) + CuI (1.1 equiv.) | Pentane (4) + THF (5) + Me₂S (1) 20 ml | −78° C.~−30° C. | 4 Hours | 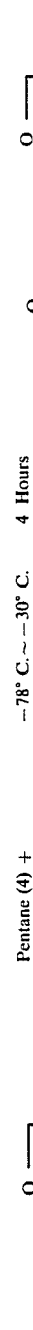 Compound [IIIG] | 30% |
| 17 | Compound [IIbA] 0.2 g |  (1.1 equiv.) + CuCN (1.1 equiv.) | THF 10 ml | −78° C.~0° C. | 1 Hour |  Compound [IIIH] | 50% |
| 18 | Compound [IIbA] 0.3 g | 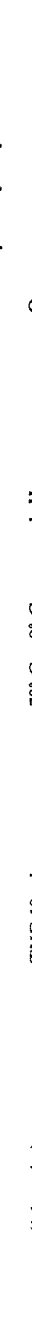 (4.0 equiv.) + CuI (1.0 equiv.) | Pentane (4) + THF (5) + Me₂S (1) 20 ml | −78° C.~−30° C. | 2 Hours |  Compound [IIII] | 50% |
| 19 | Compound [IIbB]  0.2 g |  MgCl (1.2 equiv.) + CuCN (1.5 equiv.) | THF 7 ml | 78° C.~Room temperature | 1 Hour | Compound [IIIH] | 90% |
| 20 | " | <sup>n</sup>BuMgBr (1.2 equiv.) + CuCN (1.5 equiv.) | THF 7 ml | −78° C.~Room temperature | 1 Hour | Compound [IIIA] | 80% |
| 21 | " | <sup>n</sup>BuLi (1.2 equiv.) + CuCN (1.5 equiv.) | THF (5) + Hexane (1) 6 ml | −78° C.~Room temperature | 1 Hour | Compound [IIIA] | 90% |
| 22 | " | BrMg(CH₂)₆OEE (1.2 equiv.) + | THF 7 ml | −78° C.~Room | 1 Hour | Compound [IIIB] | 70% |

TABLE 1-continued

| Example | Compound of Formula [IIb] | Compound of Formula [VI] ( ) indicates equivalents for Compound [IIb] | Reaction Conditions Solvent | Reaction Conditions Temperature | Time | Structural Formula | Compound of Formula [III] | Yields |
|---|---|---|---|---|---|---|---|---|
| 23 | " | CuCN (1.5 equiv.) BrMg(CH₂)₆OEE (1.2 equiv.) + CuCN (1.5 equiv.) | THF 10 ml | −78° C.~Room temperature | 1 Hour | | Compound [IIIB] | 60% |
| 24 | " | ⁿBuLi (2 equiv.) + CuCN (2.2 equiv.) | THF 10 ml | −78° C.~Room temperature | 1 Hour | | Compound [IIIA] | 95% |
| 25 | " | ⁿBuMgBr (2 equiv.) + CuCN (2.2 equiv.) | THF 10 ml | −78° C.~Room temperature | 1 Hour | | Compound [IIIA] | 70% |
| 26 | Compound [IIbA] 0.2 g | Et₂NH (2 equiv.) | THF 3 ml | Room temperature | 3 Hours | 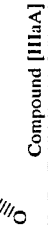 Compound [IIIaA] | | 90% |

EXAMPLE 27

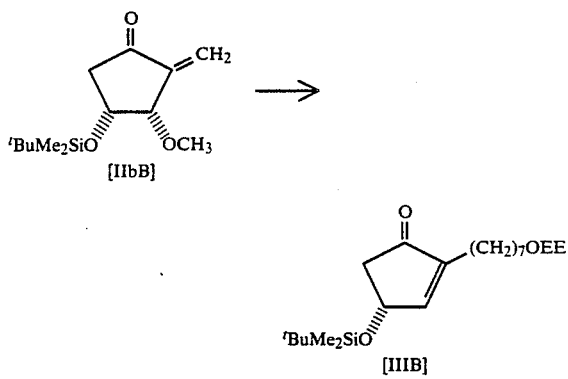

In 15 ml of tetrahydrofuran was dissolved 627 mg (7 mmol) of cuprous cyanide in an atmosphere of argon. To the solution cooled to −78° C. was added dropwise 0.34 ml (6 mmol) of EEO(CH$_2$)$_6$MgCl (0.58 mol solution in tetrahydrofuran), followed by stirring for 20 minutes. To the reaction mixture cooled to −78° C. was added dropwise 15 ml of tetrahydrofuran solution containing 1.28 g (5 mmol) of the compound (IIbB). The reaction mixture was warmed to room temperature over 1 hour. To the reaction mixture were added 30 ml of saturated aqueous solution of ammonium chloride and 30 ml of hexane, followed by stirring at room temperature for 1 hour. The organic layer was separated and the water layer was extracted with 15 ml of hexane. The organic layer was dried with anhydrous magnesium sulfate and then filtered. The filtrate was concentrated under reduced pressure. The resulting crude product was purified by silica gel chromatography. Thus there was obtained the compound (IIIB) in an amount of 1.71 g (4.3 mmol). Yield: 86%.

EXAMPLE 28

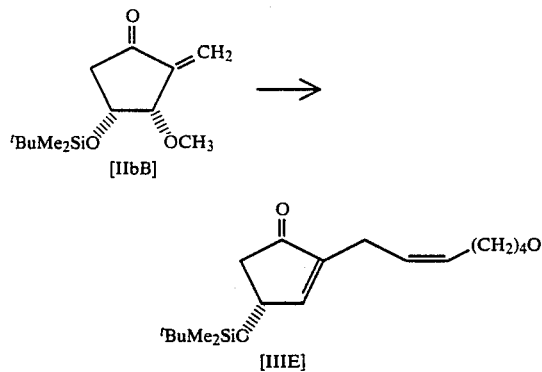

To 10 ml of diethyl ether solution containing 269 mg (9.0 mmol) of

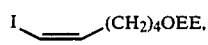

cooled to −78° C., was added dropwise 10.6 ml (18 mmol) of $^n$BuLi (1.70 mol solution in pentane), followed by stirring at −78° C. for 1 hour. This solution was added dropwise at −78° C. to 20 ml of previously prepared tetrahydrofuran solution containing 967 mg (10.8 mmol) of cuprous cyanide, followed by stirring for 15 minutes. To the reaction mixture cooled to −70° C. was added dropwise 18 ml of tetrahydrofuran solution containing 1.53 g (6 mmol) of the compound (IIbB). The reaction mixture was warmed to room temperature over 1 hour. To the reaction mixture were added 50 ml of saturated aqueous solution of ammonium chloride and 50 ml of hexane, followed by stirring at room temperature for 1 hour. The reaction product was extracted with 200 ml of hexane. The organic layer was dried with anhydrous magnesium sulfate and then concentrated. The resulting crude product was purified by silica gel chromatography. Thus there was obtained the compound (IIIE) in an amount of 2.09 g (5.28 mmol). Yield: 88%.

The following are the analytical values of the compounds (IIIB), (IIIC), (IIID), (IIIE), (IIIF), (IIIH), (III I), and (IIIaA).

Analytical values of the compound (IIIB) $^1$H-NMR (CCl$_4$, internal standard: benzene) δ0.15 (s, 6H, 2SiCH$_3$), 0.93 (s, 9H, 3SiCCH$_3$), 1.03∼1.80 (m, 16H), 2.01∼2.30 (m, 2H, C=CCH$_3$), 2.14 (dd, J=2.4, 19.2Hz, 1H), 2.59 (dd, J=6.0, 19.2Hz, 1H), 3.05∼3.67 (m, 5H), 4.55 (q, J=5.4Hz, 1H OCH(CH$_3$)O), 4.72∼4.95 (m, 1H, SiOCH), 6.88 (brs, 1H, C=CH). IR : 2920, 1710, 1250, 1080, 835 cm$^{-1}$. Rf value (silica gel thin-layer chromatography, n-hexane/diethyl ether =2/1) =0.33

Analytical values of the compound (IIIC) $^1$H-NMR (CCl$_4$, internal standard: benzene) δ0.14 (s, 6H), 0.89 (s, 9H), 0.80∼1.85 (m, 5H), 1.98∼2.32 (m, 3H), 2.58 (dd, J=5.7, 18.3Hz 1H), 4.70∼4.93 (m, 1H), 6.86 (brs, 1H).

Analytical values of the compound (IIID) $^1$H-NMR (CCl$_4$, internal standard: benzene) δ0.09 (s, 6H), 0.90 (s, 9H), 1.01∼1.90 (m, 10H), 2.00∼2.48 (m, 3H), 2.65 (dd, J=6.1, 18Hz 1H), 2.94 (brs, 2H), 3.15∼3.68 (m, 4H), 4.53 (q, J=5.1Hz, 1H), 4.70∼4.95 (m, 1H), 7.13 (brs, 1H).

Analytical values of the compound (IIIE) $^1$H-NMR (CDCl$_3$, TMS) δ0.80 (6H, s), 0.81 (9H, s), 1.07 (3H, d, J=7Hz), 1.18 (3H, t, J=6Hz), 1.3∼1.6 (4H, m), 1.7∼2.2 (2H, m), 2.19 (1H, dd, J=18Hz, 3Hz), 2.68 (1H, dd, J=18Hz, 5Hz), 2.8 (2H, m), 3.1∼3.8 (4H, m), 4.58 (1H, q, J=6Hz), 4.78 (1H, m).

Analytical values of the compound (IIIF) $^1$H-NMR (CCl$_4$, internal standard: benzene) δ0.13 (s, 6H), 0.89 (s, 9H), 1.10∼2.31 (m, 20H), 2.15 (dd, J=2.4, 18Hz, 1H), 2.59 (dd, 18, 6.0Hz, 1H), 2.66∼2.91 (m, 2H), 3.05∼3.88 (m, 4H), 4.45 (brs, 1H), 4.68∼4.92 (m, 1H), 5.15∼5.65 (m, 2H), 6.84 (brs, 1H).

Analytical values of the compound (IIIH) $^1$H-NMR (CCl$_4$, internal standard: benzene) δ0.18 (s, 6H, 2SiCH$_3$), 0.94 (s, 9H, 3SiCCH), 2.20 (dd, J=3, 18Hz), 2.64 (dd, J=6, 18Hz), 2.79∼3.03 (m, 2H, C=CCH$_2$), 4.73∼5.35 (m, 3H, SiOCH and C=CCH$_2$), 5.58∼6.08 (m, 1H, HC=CH$_2$), 6.93 (brs, 1H, (O=)CC=CH). [α]$_D^{23}$ +21.5° (C=2.74, CHCl$_3$) The optical purity was confirmed to be >99% ee by the chiral cell OD (hexane 1.0 ml/min, 230 nm), Daisel Company.

Analytical values of the compound (III I) $^1$H-NMR (CCl$_4$, internal standard: benzene) δ0.10 (s, 6H), 0.8∼1.5 (m, 18H), 2.4 (d, J=2Hz, 1H), 2.8 (2H, dd, J=17Hz, J=6Hz), 4.7 (m, 1H), 7.1 (brd, 1H) MS (m/e): [M-CH].=267 (2%), [M-$^t$Bu]=225 (11%), 169 (base peak).

Analytical values of the compound (IIIaA)
$^1$H-NMR (CCl$_4$, internal standard: benzene) δ0.20 (s, 6H), 0.96 (s, 9H), 1.06 (t, J=6.6Hz, 6H), 2.23 (dd, J=2.7, 18Hz, 1H), 2.48 (q, J=6.9Hz, 4H), 2.64 (dd, J=6.0, 18Hz, 1H), 3.14 (brs, 2H), 4.90 (brs, 1H), 7.12

(brs, 1H). $^{13}$C-NMR (CDCl$_3$) : δ205.0, 158.2, 144.7, 68.9, 47.3, 47.1, 45.6, 25.6, 17.9, 11.9, −4.8. IR (neat) : 2940, 1710, 1080, 835, 780 cm$^{-1}$. [α]+17.4° (C=1.04, CHCl$_3$), Boiling point: 141°∼143° C./0.45 mmHg

EXAMPLE 29

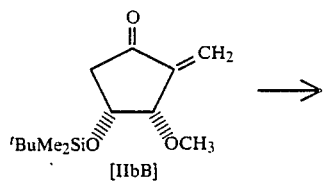

In 12 ml of tetrahydrofuran was dissolved 1.66 g (6.48 mmol) of the compound (IIbB). To this solution was slowly added 1.32 ml (12.8 mmol, 2 equivalents) of diethylamine. After stirring at room temperature for 12 hours, 10 ml of water was added, and the reaction product was extracted with two 10 ml portions of diethyl ether. The organic layer was washed with a saturated aqueous solution of sodium chloride and then dried with anhydrous magnesium sulfate. The solvent was distilled away and the resulting oily substance was purified by silica gel chromatography (20 g, hexane : ethyl acetate =2:1→1:2). Thus there was obtained the compound (IIIaA) in an amount of 1.79 g. Yield: 93%.

The compound (IIIaA) was found to have the same property values as the compound (IIIaA) obtained in Example 26.

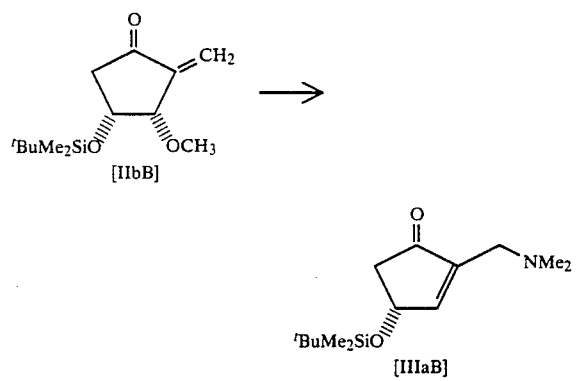

EXAMPLE 30

In 4 ml of tetrahydrofuran was dissolved 500 mg (2.0 mmol) of the compound (IIbB). To this solution was added 0.36 g (4 mmol) of 50% aqueous solution of dimethylamine, followed by stirring at room temperature for 18 hours. To the reaction mixture were added 50 ml of saturated aqueous solution of sodium chloride, and the reaction product was extracted with two 5 ml portions of ethyl acetate. The organic layer was dried with anhydrous magnesium sulfate and the solvent was distilled away. There was obtained 520 mg of oily substance. It was purified by silica gel chromatography (10 g, hexane : ethyl acetate =1:1→ethyl acetate). Thus there was obtained the compound (IIIaB) in the oily form in an amount of 80 mg. Yield: 15%.

Analytical values of the compound (IIIaB) $^1$H-NMR (CCl$_4$, TMS standard) δ0.13 (s, 6H), 0.91 (s, 9H), 2.25 (s, 6H), 2.29 (dd, J=18Hz, J=2Hz, 1H), 2.79 (dd, J=18Hz, J=6Hz, 1H), b 3.09 (brs, 2H), 4.94 (dt, J=6Hz, 2Hz, 1H), 7.27 (m, 1H). IR : 2930, 2900, 2840, 2800, 2750, 1700, 1250 cm$^{-1}$ MS (m/e): 269 (9, M.), 254 (6), 44 (base peak). [α]$_D^{23}$ +24 72° (C=0.36, CHCl$_3$)

EXAMPLE 31

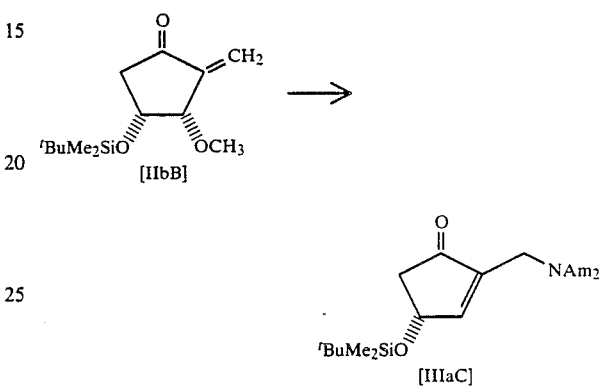

In 4 ml of tetrahydrofuran was dissolved 500 mg (2.0 mmol) of the compound (IIbB). To this solution was added 630 mg of diamylamine, followed by stirring at room temperature for 42 hours. To the reaction mixture was added 50 ml of saturated aqueous solution of sodium chloride, and the reaction product was extracted with two 5 ml portions of ethyl acetate. The organic layer was dried with anhydrous magnesium sulfate and the solvent was distilled away. There was obtained 980 mg of oily substance. It was purified by silica gel chromatography (30 g, hexane : ethyl acetate =20:1). Thus there was obtained the compound (IIIaC) in the oily form in an amount of 195 mg. Yield: 26%. The raw material was recovered in an amount of 281 mg. Recovery: 56%

Analytical values of the compound (IIIaC) $^1$H-NMR (CCl$_4$, TMS standard) δ0.13 (s, 6H), 0.91 (s, 9H), 0.8∼1.0 (m, 10H), 1.0∼1.7 (m, 8H), 1.9∼2.5 (m, 5H), 2.77 (dd, J=18Hz, J=6Hz, 1H), 3.14 (brs, 2H), 4.90 (dt, J=6Hz, 2Hz, 1H), 7.26 (m, 1H). IR : 2940, 2900, 2840, 2770, 1700, 1250 cm$^-$MS (m/e): 381 (0.5, M$^+$), 324 (base peak). [α]$_D^{25}$ +16.5° (C=1.018, CHCl$_3$)

EXAMPLE 32

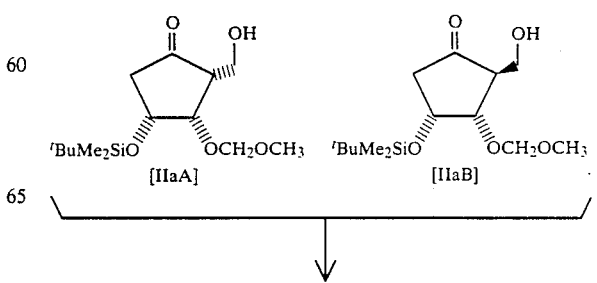

-continued

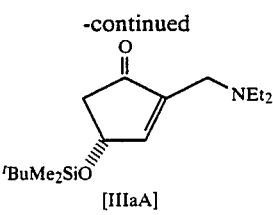
[IIIaA]

To 100 ml of methylene chloride solution containing 10.0 g (32.8 mmol) of a mixture of the compounds (IIaA) and (IIaB) was added 12.8 ml (91.6 mmol) of triethylamine. To the reaction mixture cooled to 0° C. was added dropwise with stirring 3.6 ml (45.8 mmol) of methylsulfonyl chloride, followed by stirring at 0° C. for 40 minutes. 50 ml of a saturated aqueous solution of sodium hydrogen carbonate was added. The reaction mixture was warmed to room temperature and stirred for 1 hour. Further, 7.8 ml (76.3 mmol) of diethylamine was added, followed by stirring at room temperature for 12 hours. The reaction product was extracted with three 30 ml portions of ethyl acetate. The organic layer was dried with anhydrous magnesium sulfate and filtered. The solvent was distilled away from the filtrate under reduced pressure. The resulting crude product was purified by silica gel chromatography. Thus there was obtained the compound (IIIaA) in an amount of 7.7 mg (25.9 mmol). Yield: 79%.

The compound (IIIaA) was found to have the same property values as the compound (IIIaA) obtained in Example 26.

EXAMPLE 33

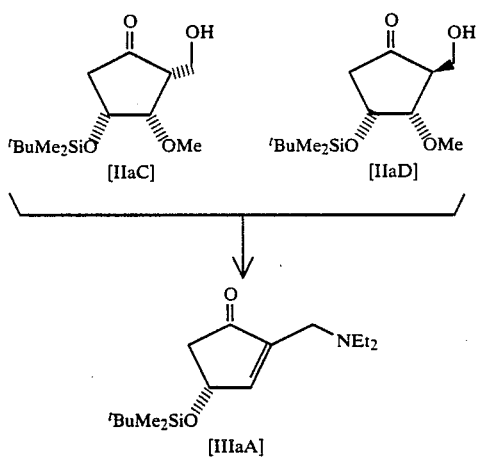

To 27 ml of methylene chloride solution containing 3.72 g (14.4 mmol) of a mixture of the compounds (IIaC) and (IIaD) was added 9.35 ml (72 mmol) of triethylamine. To the reaction mixture was added dropwise with stirring 1.66 ml (21 mmol) of methanesulfonyl chloride, followed by stirring at 0° C. for 1 hour. 20 ml of a saturated aqueous solution of sodium hydrogen carbonate was added. The reaction mixture was warmed to room temperature and stirred for 1 hour. Further, 2.81 ml (29 mmol) of diethylamine was added, followed by stirring at room temperature for 12 hours. The reaction product was extracted with two 100 ml portions of ethyl acetate. The organic layer was dried with anhydrous magnesium sulfate and filtered. The solvent was distilled away from the filtrate under reduced pressure. Thus there was obtained the compound (IIIaA) in an amount of 3.20 g. Yield: 83%.

The compound (IIIaA) was found to have the same property values as the compound (IIIaA) obtained in Example 26.

EXAMPLE 34

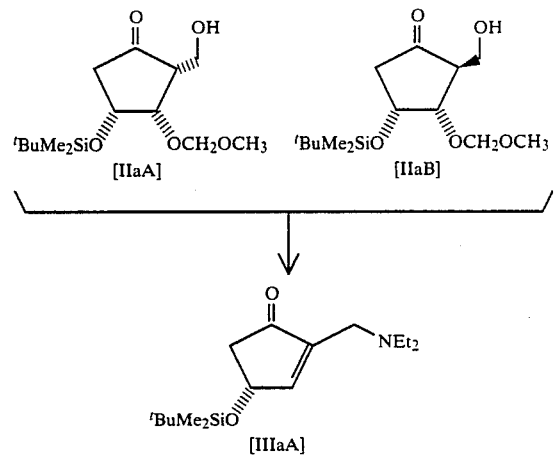

To 100 ml of methylene chloride solution containing 8.35 g (30.5 mmol) of a mixture of the compounds (IIaA) and (IIaB) was added 12.8 ml (91.6 mmol) of triethylamine. To the reaction mixture cooled to 0° C was added dropwise with stirring 3.6 ml (45.8 mmol) of methylsulfonyl chloride, followed by stirring at 0° C for 40 minutes. 50 ml of a saturated aqueous solution of sodium hydrogen carbonate was added. The reaction mixture was warmed to room temperature and stirred for 1 hour. Further, 7.8 ml (76.3 mmol) of diethylamine was added, followed by stirring at room temperature for 12 hours. The reaction product was extracted with three 30 ml portions of ethyl acetate. The organic layer was dried with anhydrous magnesium sulfate and filtered. The solvent was distilled away from the filtrate under reduced pressure. The crude product was purified by silica gel column chromatography. Thus there was obtained the compound (IIIaA) in an amount of 8.24 g (27.7 mmol). Yield: 91%.

The compound (IIIaA) was found to have the same property values as the compound (IIIaA) obtained in Example 26.

EXAMPLE 35

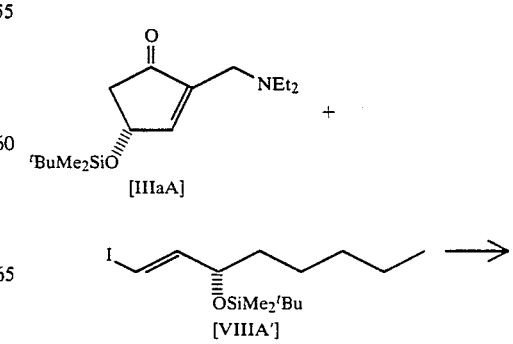

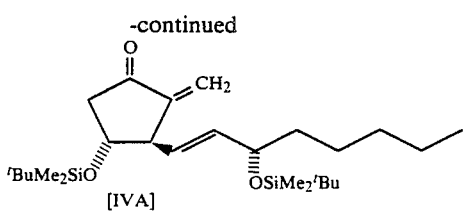

To 17.5 ml of diethyl ether solution, cooled at −78° C., containing 2.32 g (6.3 mmol) of the compound (VIIIA') was added 12.6 mmol (7.42 ml off 1.70 M pentane solution) of t-butyl lithium with stirring. The reaction mixture was heated to −40° C. over 1 hour. The reaction mixture was added cooled again to −78° C. To the reaction mixture was added 6.6 mol (18.53 ml of 0.34 M tetrahydrofuran solution) 2-thienylcyano copper lithium of the formula:

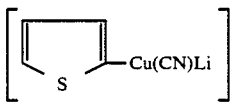

After stirring at −78° C. for 20 minutes, 21 ml of a tetrahydrofuran solution containing 1.56 g (5.25 mmol) of the compound (IIIaA) was slowly added dropwise. The reaction mixture was stirred at −78° C. for 20 minutes. The reaction mixture was poured into a mixture of saturated ammonium chloride solution (100 ml) and n-hexane (100 ml). Stirring was continued until the organic layer became clear. The organic layer was separated and the water layer was extracted with 50 ml of n-hexane. The n-hexane extract was added to the organic layer. The organic layer was dried with anhydrous magnesium sulfate and filtered. The solvent was distilled away from the filtrate under reduced pressure. The crude product was purified by silica gel column chromatography. Thus there was obtained the compound (IVA) in an amount of 2.32 g (4.98 mmol). Yield: 95%.

The following are the analytical values of the compound (IVA).

$^1$H $^1$H-NMR (CCl$_4$, PhH standard) δ0.04 and −0.02 (2s, 6H), 0.0 (s, 6H), 0.98 (brs, 21H), 1.20∼1.80 (m, 8H), 2.30 and 2.56 (2dd, J=7.8, 18.6Hz, J=7.1, 18.6Hz, 2H), 3.09∼3.40 (m, 1H), 3.92∼4.30 (m, 2H), 5.12 (brs, 1H), 5.30∼5.83 (m, 2H), 5.99 (brs, 1H).

$^{13}$C-NMR (CDCl$_3$), δ202.2, 147.0, 137.7, 127.4, 118.5, 73.0, 72.5, 54.5, 46.9, 38.4, 31.8, 25.8, 25.7, 24.9, 24.6, 22.5 18.1, 17.9, 13.9, ∼4.4, ∼4.8. IR (neat): 2930, 1730, 1640, 1470, 1250, 1110, 840, 780 cm$^{-1}$ [α]$_D^{25}$ 46.1° (C=0.781, CHCl$_3$)

EXAMPLE 36

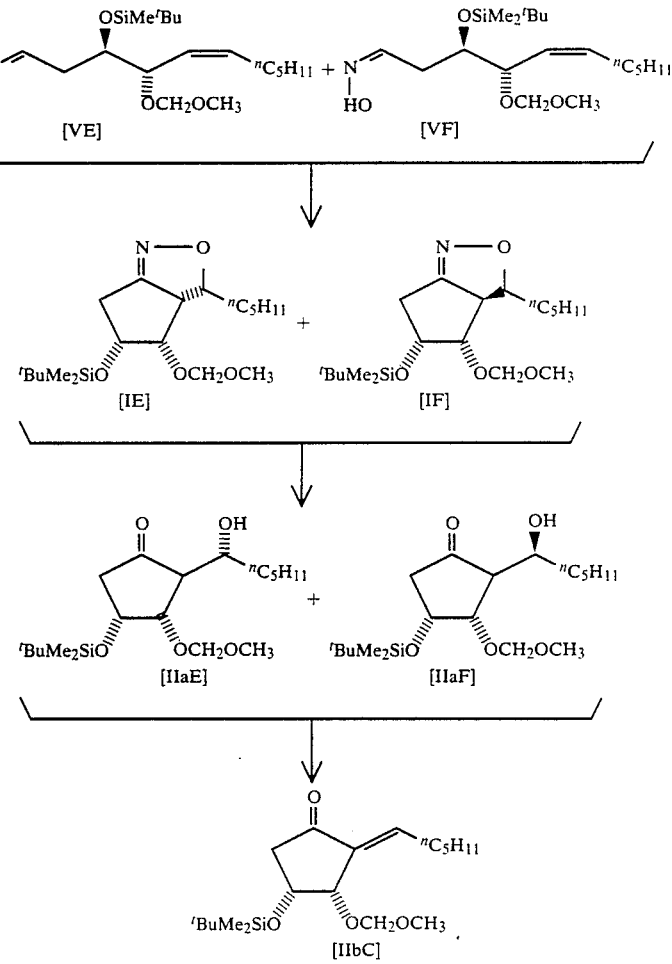

At first, 1.95 g (5.34 mmol) of a mixture of the compounds (VE) and (VF) was reacted in the same manner as in Example 1. There was obtained 840 mg (2.34 mmol) of an oily mixture of the compounds (IE) and (IF). Yield: 44%.

Then, a mixture of the compounds (IE) and (IF) was reacted in the same manner as in Example 2. There was obtained 740 mg (2.0 mmol) of an oily mixture of the compounds (IIaE) and (IIaF). Yield: 86%.

Further, a mixture of the compounds (IIaE) and (IIaF) was reacted in the same manner as in Example 3. There was obtained 576 mg of the compound (IIbC). Yield: 82%.

The analytical values are given below.

Analytical values of the mixture of (IE) and (IF) $^1$H-NMR (CCl$_4$, internal standard: benzene) δ0.14 (s, 6H), 0.87 (s, 9H), 0.70~1.12 (m, 3H), 1.13~1.70 (m, 8H), 2.40~2.63 (m, 2H), 3.30 (s, 3H), 3.82~4.12 and 4.20~4.75 (m, 6H). Rf value: (hexane/diethyl ether =3/1) =0.36

Analytical values of the mixture of (IIaE) and (IIaF) $^1$H-NMR (CCl$_4$, internal standard: benzene) δ0.17 (s, 6H), 0.90 (s, 9H), 0.76~1.13 (m, 3H), 1.16~1.75 m, 8H), 2.25~2.50 (m, 3H), 3.10 (brs, 1H), 3.34 (s, 3H), 3.85~4.12 and 4.40~4.57 (m, 2H), 4.28 (dd, J=3.0, 8.0Hz, 1H), 4.55 and 4.76 (2d, J=6.0Hz, 2H).

Rf value: (hexane/diethyl ether =1/1)=0.17 Analytical values of the compound (IIbC) $^1$H-NMR (CCl$_4$, internal standard: benzene) δ0.19 (s, 6H)(, 0.99 (s, 9H(, 0.79~1.15 (m, 6H), 1.16~1.75 (m, 6H), 3.32 (s, 3H), 403~4.38 (m, 1H) 4.45~4.85 (m, 3H), 6.56 (t, J=8.0Hz, 1H). Rf value: (hexane/diethyl ether =3/1)=0.41

EXAMPLE 37

There was obtained 2.8 g (9.1 mmol) of the yellowish oily compound (IIIaD). Yield: 65%.

The analytical values are given below.

Analytical values of the mixture of (IG) and (IH) $^1$H-NMR (CCl$_4$, internal standard: benzene) 0.13 (s, 6H), 0.89 (s, 9H), 1.18~2.12 (m, 3H), 2.23~2.65 (m, 2H), 3.28 (s, 3H), 3.23~4.65 (m, 4H), 4.35~4.64 (m, 2H). Rf value: (hexane/diethyl ether =1/1) =0.36

Analytical values of the compound (IIIaD) $^1$H-NMR (CCl$_4$, internal standard: benzene) δ0.14 (s, 6H), 0.89 (s, 9H), 0.99 (t, J=6.9Hz, 6H), 1.70~2.60 (m,4H), 2.41 (q, J=6.9Hz, 4H), 3.02 (s, 3H), 3.28 (brs, 2H), 4.33~4.65 (m, 1H), 6.68 (brs, 1H). Rf value: (hexane/diethyl ether =1/2) =0.3

What is claimed is:

1. A substituted cyclopentanone or cyclohexanone compound represented by the formula (IIIa):

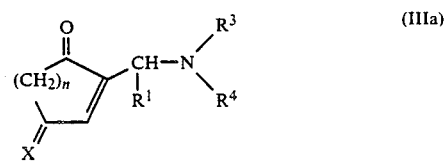

wherein X denotes (α-OZ, β-H) or (α-H, β-OZ); Z denotes a hydrogen atom or a protective group for the hydroxyl group; R$^1$ denotes a hydrogen atom, a C$_{1-10}$ alkyl group, alkenyl group, alkynyl group, or phenyl group, or a member selected from the group consisting of

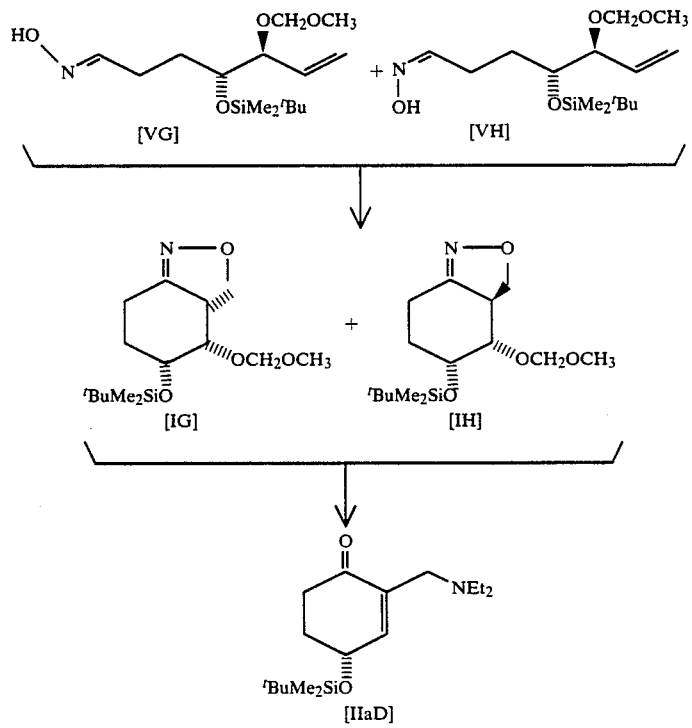

At first, 6.4 g (20 mmol) of a mixture of the compounds (VG) and (VH) was reacted in the same manner as in Example 1. There was obtained 4.4 g (14 mmol) of a yellowish oily mixture of the compounds (IG) and (IH). Yield: 70%.

Then, a mixture of the compounds (IG) and (IH) was reacted in the same manner as in Examples 2, 3 and 27.

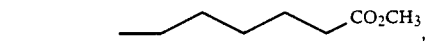

-continued

![structure: CH3-CH2-CH=CH-CH2-CH2-CH2-OTHP],

![structure: CH3-CH2-CH2-CH=CH-CO2CH3],

![structure: with OSi(CH3)2tBu],

![structure: CO2CH3, labeled allene],

![structure: S-CH2-CO2CH2C6H5],

![structure: O-CH2-CO2CH3],

![structure: S-CH2CH2-CO2CH3],

![structure: alkyne-CH2CH2-OEE],

![phenyl-O-CH2-CO2CH3], ![chlorophenyl], and

![phenyl-CH2CH2CH2-CO2CH3]

wherein THP denotes a tetrahydropyranyl group, $^t$Bu denotes a tertiary butyl group and EE denotes an ethoxy ethyl group; $R^3$ and $R^4$ each denotes a $C_{1-10}$ alkyl group or phenyl group, or a member selected from the group consisting of a p-chlorobenzyl group and a p-chlorophenyl group, $R^3$ and $R^4$ being the same or different from each other, and n is 1 or 2.

2. The compound as defined in claim 1, wherein said alkyl substituted or unsubstituted $C_{1-10}$ alkyl group, alkenyl group, alkynyl group, or phenyl group denoted by $R^1$ which is a member selected from the group consisting of a methyl group, ethyl group, n-pentyl group, ![structure: long chain with double bond], and ![phenyl ring]

3. The compound as defined in claim 1, wherein $R^3$ and $R^4$ each denotes a member selected from the group consisting of a methyl group, ethyl group, n-propyl group, i-propyl group, amyl group, benzyl group, p-chlorobenzyl group, phenyl group, and p-chlorophenyl group.

4. The compound as defined in claim 1, wherein Z denotes a member selected from the group consisting of a hydrogen atom, trimethylsilyl group, t-butyldimethylsilyl group, methoxymethyl group, benzyloxymethyl group, trityl group, and tetrahydropyranyl group.

5. The compound as defined in claim 2, wherein $R^3$ and $R^4$ each denotes a member selected from the group consisting of a methyl group, ethyl group, n-propyl group, i-propyl group, amyl group, benzyl group, p-chlorobenzyl group, phenyl group, and p-chlorophenyl group.

6. The compound as defined in claim 5, wherein Z denotes a member selected from the group consisting of a hydrogen atom, trimethylsilyl group, t-butyldimethylsilyl group, methoxymethyl group, benzyloxymethyl group, trityl group, and tetrahydropyranyl group.

7. The compound as defined in claim 1, wherein said compound is:

![cyclopentenone with CH2NEt2 and $^t$BuMe2SiO substituents].

8. The compound as defined in claim 1, wherein said compound is:

![cyclopentenone with CH2NMe2 and $^t$BuMe2SiO substituents].

9. The compound as defined in claim 1, wherein said compound is:

![cyclopentenone with CH2NAm2 and $^t$BuMe2SiO substituents].

10. The compound as defined in claim 1, wherein said compound is:

![cyclohexenone with CH2NEt2 and $^t$BuMe2SiO substituents].

* * * * *